United States Patent [19]

Perego et al.

[11] Patent Number: 5,672,799
[45] Date of Patent: Sep. 30, 1997

[54] PROCESS FOR THE PREPARATION OF CUMENE

[75] Inventors: Carlo Perego, Carnate; Giannino Pazzuconi, Pavia; Gianni Girotti, Bologna; Giuseppe Terzoni, Piacenza, all of Italy

[73] Assignees: Eniricerche S.p.A., Milan; Enichem Synthesis S.p.A., Palermo, both of Italy

[21] Appl. No.: 683,740

[22] Filed: Jul. 17, 1996

Related U.S. Application Data

[63] Continuation of Ser. No. 257,151, Jun. 9, 1994, abandoned.

[30] Foreign Application Priority Data

Jun. 16, 1993 [IT] Italy .................. MI93A1295

[51] Int. Cl.$^6$ .................................................. C07C 2/66
[52] U.S. Cl. ............................... 585/467; 585/446
[58] Field of Search ............................. 585/446, 453, 585/467

[56] References Cited

U.S. PATENT DOCUMENTS

| | | | |
|---|---|---|---|
| 3,308,069 | 3/1967 | Wadlinger et al. | 252/455 |
| 4,891,458 | 1/1990 | Innes et al. | 585/323 |
| 5,081,323 | 1/1992 | Innes et al. | 585/449 |

FOREIGN PATENT DOCUMENTS

| | | |
|---|---|---|
| 0 439 632 | 8/1991 | European Pat. Off. . |
| 0 538 518 | 4/1993 | European Pat. Off. . |

*Primary Examiner*—Ponnathapura Achutamurthy
*Attorney, Agent, or Firm*—Oblon, Spivak, McClelland, Maier & Neustadt, P.C.

[57] ABSTRACT

Process for the preparation of cumene by the alkylation of benzene with propylene, catalyzed by zeolite Beta into which certain quantities of suitable alkaline, alkaline-earth or metallic cations have been introduced by ion exchange.

7 Claims, No Drawings

PROCESS FOR THE PREPARATION OF CUMENE

This application is a Continuation of application Ser. No. 08/257,151, filed on Jun. 9, 1994, now abandoned.

The present invention relates to a procedure for the preparation of cumene by the alkylation of benzene with propylene. This procedure is carried out in the presence of zeolite Beta into which certain quantities of suitable alkaline, earth-alkaline or metallic cations have been introduced by means of ion exchange. Cumene or isopropylbenzene is mainly used for the production of phenol and acetone. The synthesis method, which is the most widely used at the moment to obtain it, is the condensation of benzene with propylene catalyzed by phosphoric acid on infusorial earth.

Although this catalyst is not expensive and causes the formation of small quantities of polyalkylates as by-products, it is corrosive and consequently creates considerable problems relating to the plant; in addition, during the process, it is necessary to add an exact dosage of water to the feeding to obtain a high reactivity of the catalyst which must also remain constant for the required time. This catalyst moreover cannot be regenerated and therefore creates problems for its disposal.

Another synthesis method industrially applied uses a slurry as condensation catalyst, containing aluminium trichloride and hydrochloric acid. This process has problems of disposal and corrosion similar to the previous method, and in addition the catalyst is difficult to separate from the mixture of products which have a lower purity than those obtained using phosphoric acid as catalyst.

To avoid these inconveniences condensation processes have been proposed using a zeolite as catalyst.

The use of ZSM-5-type zeolites is described for example in U.S. Pat. No. 4,292,457 which discloses that a boralite with a ZSM-5 type structure is capable of catalyzing the alkylation of benzene with propylene. This type of zeolitic system however, perhaps owing to channels which are too small, only enables the production of cumene with a rather low selectivity.

On the other hand a zeolite with wide pores such as ZSM-12 has a good selectivity for cumene but a low activity and it is therefore necessary to operate at high temperatures. These conditions however also favour undesirable reactions, such as the cracking of the cumene, for example, which can cause a rapid deactivation of the catalyst.

There are also numerous patents which describe, for the synthesis of cumene, the use of zeolites of the Faujasite type suitably modified by special treatments such as stabilization by treatment with vapour and exchange with rare earth.

In particular the most widely used is the Y type zeolite. This is characterized by a good activity at temperatures of between 130° C. and 180° C. and a good selectivity for the desired product. This selectivity however greatly decreases with the increasing conversion of the benzene and it is therefore necessary to operate with quite high molar ratios between benzene and propylene in the feeding which limit the polyalkylations reactions. Such high ratios obviously involve high costs for recycling the benzene. EP 432814 and EP 439632 claim a procedure for the alkylation of aromatic and alkylaromatic compounds with olefins containing from 2 to 4 carbon atoms using zeolite Beta as catalyst mainly or totally in acid form, or in which the majority of the cation "sites" is occupied by hydrogen ions. The beta zeolites used in these processes can be represented by the general formula:

wherein y is between 5 and 100, w is less than or equal to 4, M is a metallic ion, n is the valence of M and x preferably has a value lower than 0.2.

We have now found a procedure for the preparation of cumene by the alkylation of benzene with propylene using as catalyst beta zeolite into which suitable quantities of particular alkaline, alkaline-earth or metallic cations have been introduced by means of ion exchange. With this catalyst higher values of selectivity are obtained compared to what is described in the known art, without favouring, in particular, polyalkylation reactions.

The present invention therefore relates to a procedure for the preparation of cumene from benzene and propylene using as reaction catalyst a zeolite Beta having the following formula:

wherein y is between 5 and 100, w is less than or equal to 4, $M=Na^+$, $K^+$, $Ca^{2+}$ or $Ni^{2+}$ and x has a value of between 0.25 and 0.50.

The water content of the zeolite depends on the synthesis method used and the treatment after the preparation.

This catalytic system, characterized by a considerable content of metallic ions, has a good activity and molar selectivity to cumene of the converted benzene which is higher than that of the zeolite Beta mainly or totally in acid form, i.e. having an x co-efficient value which is less than 0.2. This selectivity datum, hereinafter indicated as [C9]/[C6], is a measurement of the capacity of the catalyst of favouring the formation of the monoalkylation product: the zeolite Beta modified with suitable quantities of metallic ions gives better selectivity values with a reduction of as much as 50% in the formation of polyalkylation products.

When the metallic cation is in particular potassium, also the molar selectivity to cumene of the converted propylene [C9]/[C3−] is improved with respect to the results of the prior art. This shows that in the alkylation process of benzene with propylene the use of a zeolite Beta modified by the introduction of potassium ions in suitable quantities discourages the formation of undesired oligomeric by-products.

The zeolites Beta modified by the introduction of suitable quantities of metallic ions are prepared as described in U.S. Pat. No. 3,308,069, a subsequent exchange with ammonium and calcination to obtain the beta zeolite in a completely acid form, a further exchange to introduce calibrated quantities of an ion selected from $Na^+$, $K^+$, $Ca^{2+}$ or $Ni^{2+}$. The exchange is carried out using the known techniques, as described by R. P. Townsend in "Ion exchange in zeolites", Studies Surf. Scien. Cat., vol.58, pages 359–390, 1991. The sodium, potassium, calcium and nickel salts which can be used for the exchange are for example the corresponding acetates, nitrates and chlorides.

The alkylation process of benzene with propylene catalyzed by zeolite Beta modified by the introduction of suitable quantities of metallic ions can be carried out in a gaseous phase, or in a liquid or mixed phase, and in batch, semicontinuous or continuous. The reaction temperature is selected within the range of 150° C. and 300° C., preferably between 150° and 200° C.; the pressure is between 10 and 50 atm, preferably between 25 and 35 atm, and the total WHSV feeding rate of the reagents is selected within the range of 0.1 and 200 hours$^{-1}$, preferably between 1 and 10 hours$^{-1}$.

The catalysts can be used in a mixture with suitable binders such as silicon, aluminium, zirconium, magnesium oxides or natural clays and combinations of these.

The zeolite and binder are mixed in relative quantities of between 50:50 and 95:5, preferably between 70:30 and 90:10. The mixture of the two components is then consolidated into the final form required for the catalyst, for example into cylindrical extruded form. In the procedure for the preparation of the cumene the molar feeding ratio between benzene and propylene can vary from 2 to 30 and is preferably between 4 and 15. The reagents can be fed to the reactor either from the bottom towards the top or viceversa. The heat which develops during the process can be controlled by the feeding of inert paraffins at different points of the catalytic bed.

The regeneration of the catalyst is obtained by thermal treatment in air, for example at a temperature of between 500° C. and 650° C.

The following examples illustrate the preparation of cumene using zeolite Beta as catalyst modified by the introduction of suitable quantities of sodium and potassium (ex. 8, 9, 10, 12 and 13), a zeolite Beta in a totally acid form containing sodium, directly from the synthesis, in a quantity which is lower than that used in the present invention (ex. 7). On comparing the data it can be clearly seen that the modified zeolite Beta gives a better performance with respect to the selectivity to cumene of converted benzene, and when the zeolite Beta specifically contains potassium in suitable quantities even better selectivity values to cumene of converted propylene can be obtained.

EXAMPLE 1

Preparation of the zeolite Beta Containing $Na^+$ Directly from the Synthesis 58.8 g of tetraethylammoniumhydroxide at 40% by weight in an aqueous solution and 1.9 g of sodium aluminate are added to 58.4 g of demineralized water. The mixture is heated to about 80° C. and is left under stirring until complete dissolution. The limpid solution thus obtained is added to 37.5 g of Ludox HS colloidal silica at 40% by weight. A homogeneous suspension is obtained having pH=14, which is charged into a steel autoclave and left to crystallize under hydrothermal conditions at 150° C. for 10 days, under static conditions and at autogenous pressure. The crystallized product is separated by filtration, washed, dried for 1 hour at 120° C., calcinated for 5 hours at 550° C. Upon chemical analysis, the zeolite Beta thus obtained has the following composition expressed as a molar ratio:

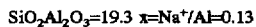

$SiO_2/Al_2O_3=19.3 \quad x=Na^+/Al=0.13$

EXAMPLE 2

Preparation of zeolite Beta in $H^+$ Form

The zeolite Beta obtained in example 1 is exchanged into acid form by treatment with ammonium acetate and subsequent calcination at 550° C. for 5 hours.

The product was characterized by X-ray diffraction from powders.

EXAMPLE 3

The zeolite Beta in acid form obtained according to example 2 is exchanged with sodium acetate by putting a dispersion at 10% weight/weight of zeolite in demineralized water in contact with a quantity of sodium acetate in such a way that the molar ratio $Na^+/Al$ is equal to 0.55 and leaving the resulting mixture at reflux temperature for 24 hours. At the end the zeolite is washed with water, filtered and calcined at 550° C. for 5 hours. The zeolite Beta thus obtained contains sodium in such a quantity that the ratio in moles $Na^+/Al$, or the x co-efficient, is equal to 0.5.

EXAMPLE 4

The zeolite Beta in acid form obtained according to example 2 is exchanged with potassium acetate by putting a dispersion at 10% weight/weight of zeolite in demineralized water in contact with a quantity of potassium acetate in such a way that the molar ratio $K^+/Al$ is equal to 0.5 and leaving the resulting mixture at reflux temperature for 24 hours. At the end the zeolite is washed with water, filtered and calcinated at 550° C. for 5 hours. The zeolite Beta thus obtained contains potassium in such a quantity that the ratio in moles $K^+/Al$ is equal to 0.36.

EXAMPLE 5

The zeolite Beta in acid form obtained according to example 2 is exchanged with potassium acetate by putting a dispersion at 10% weight/weight of zeolite in demineralized water in contact with a quantity of potassium acetate in such a way that the molar ratio $K^+/Al$ is equal to 0.4 and leaving the resulting mixture at reflux temperature for 24 hours. At the end the zeolite is washed with water, filtered and calcinated at 550° C. for 5 hours. The zeolite Beta thus obtained contains potassium in such a quantity that the ratio in moles $K^+/Al$ is equal to 0.25.

EXAMPLE 6 zeolite Beta in acid form, prepared as in example 2 is charged as catalyst into a 0.5 l autoclave equipped with a magnetic stirrer and electric heating. A vacuum is created in the system and 400 cc of benzene are then charged. The temperature is brought to 150° C., under stirring, and liquid propylene is then charged by thrust and overpressure of nitrogen until an internal pressure is reached in the autoclave of 30 bar. The quantity of propylene charged is such that the molar ratio $[C6]/[C3=]$ is equal to 7.4. 1 hour after the charging a quantity of the product is removed, directly from the autoclave under pressure and at temperature, which is analyzed by gas chromatograph using a Wide-Bore capillary column with a 100% Methylsilicon phase, with a temperature regulated up to 220° C. and a F.I.C. detector.

The results are shown hereunder:

coversion C3-=78.9% molar selectivity $[C9]/[C3=]=92.1\%$ molar selectivity $[C9]/[C6]=95.4\%$

Molar selectivity $[C9]/[C3=]$ refers to the molar fraction of propylene reacted to cumene with respect to the total reacted propylene; molar selectivity $[C9]/[C6]$ refers to the molar fraction of benzene reacted to cumene with respect to the total reacted benzene.

EXAMPLE 7

The same procedure is carried out as in example 6 charging 0.4 g of zeolite prepared as in example 1 and removing the product after 2 hours of reaction.

The results are shown hereunder:

molar selectivity $[C9]/[C3=]=91.3\%$ molar selectivity $[C9]/[C6]=96.6\%$

EXAMPLE 8

The same procedure is carried out as in example 6 charging 0.4 g of zeolite prepared as in example 3 and removing the product after 4 hours of reaction.

The results are shown hereunder:

conversion C3-=76.7% molar selectivity [C9]/[C3-]=92.1% molar selectivity [C9]/[C6]=97.2%

EXAMPLE 9

The same procedure is carried out as in example 6 charging 0.4 g of zeolite prepared as in example 4 and removing the product after 4 hours of reaction.

The results are shown hereunder:

conversion C3-=78.5% molar selectivity [C9]/[C3-]=92.1% molar selectivity [C9]/[C6]=97.6%

EXAMPLE 10

The same procedure is carried out as in example 6 charging 0.4 g of zeolite prepared as in example 5 and removing the product after 3 hours of reaction.

The results are shown hereunder:

conversion C3-=81.9% molar selectivity [C9]/[C3-]=92.1% molar selectivity [C9]/[C6]=97.1%

EXAMPLE 11

The same procedure is carried out as in example 6, except for the temperature which is increased to 180° C., charging 0.4 g of zeolite prepared as in example 2 and removing the product after 1 hour of reaction.

The results are shown hereunder:

conversion C3-=99.9% molar selectivity [C9]/[C3-]=91.2% molar selectivity [C9]/[C6]=95.6%

EXAMPLE 12

The same procedure is carried out as in example 6, at a temperature of 180° C., charging 0.4 g of zeolite prepared as in example 5 and removing the product after 1 hour of reaction.

The results are shown hereunder:

conversion C3-=98.8% molar selectivity [C9]/[C3-]=91.4% molar selectivity [C9]/[C6]=96.5%

EXAMPLE 13

The same procedure is carried out as in example 6, at a temperature of 180° C., charging 0.4 g of zeolite prepared as in example 4 and removing the product after 1 hour of reaction.

The results are shown hereunder:

conversion C3-=91% molar selectivity [C9]/[C3-]=92.3% molar selectivity [C9]/[C6]=96.5%

We claim:

1. A process for the preparation of cumene comprising the steps of:

reacting benzene and propylene in the presence of a zeolite Beta catalyst having the formula:

$$(x/n)M.(1.0-x) H^+ \cdot AlO_2 \cdot y\ SiO_2 \cdot w\ H_2O$$

wherein y is from 5 to 100, w is less than or equal to 4, $M=Na^+$, $K^+$, $Ca^{2+}$ or $Ni^{2+}$ and x has a value of from 0.25 to 0.50; carrying out said reaction at a temperature of from 150° to 300° C., a pressure of from 10 to 50 atm and a total WHSV feeding rate of reagents of from 0.1 to 200 $hrs^{-1}$.

2. Procedure according to claim 1 wherein the temperature is from 150° to 200° C.

3. Procedure according to claim 1 wherein the pressure is from 25 to 30 atm.

4. Procedure according to claim 1 wherein the total WHSV feeding rate of the reagents is from 1 to 110 $hrs^{-1}$.

5. Procedure according to claim 1 wherein the molar ratio between benzene and propylene is from 2 to 30.

6. Procedure according to claim 5 wherein the molar ratio between benzene and propylene varies from 4 to 15.

7. Procedure according to claim 1 wherein the zeolite Beta is used in a mixture with one or more binders selected from the group consisting of silicon, aluminium, zirconium, magnesium oxides and natural clays.

* * * * *